United States Patent [19]

Stoopak et al.

[11] 4,366,145
[45] Dec. 28, 1982

[54] SOFT GELATIN CAPSULE WITH A LIQUID ERGOT ALKALOID CENTER FILL SOLUTION AND METHOD OF PREPARATION

[75] Inventors: Samuel B. Stoopak, West Caldwell; Saul S. Kornblum, Springfield; Allen L. Jacobs, Randolph, all of N.J.

[73] Assignee: Sandoz, Inc., East Hanover, N.J.

[21] Appl. No.: 277,980

[22] Filed: Jun. 24, 1981

[51] Int. Cl.$^3$ .................... A61K 9/48; A61K 31/48
[52] U.S. Cl. ........................................ 424/37; 424/261
[58] Field of Search ................................ 424/37, 261

[56] References Cited

U.S. PATENT DOCUMENTS

| | | | |
|---|---|---|---|
| 2,269,145 | 1/1942 | Cultor et al. | 424/261 |
| 2,870,062 | 1/1959 | Stanley et al. | 424/37 |
| 3,632,742 | 1/1972 | Eckert et al. | 424/37 |
| 3,784,684 | 1/1974 | Bossert et al. | 424/37 |
| 3,849,562 | 11/1974 | Richardson | 424/261 |
| 3,887,705 | 6/1975 | Serre et al. | 424/261 |
| 4,002,718 | 1/1977 | Gardeila et al. | 424/37 |
| 4,078,065 | 3/1978 | Franz | 424/261 |
| 4,088,750 | 5/1978 | Cresswell et al. | 424/37 |
| 4,138,565 | 2/1979 | Ehrhard et al. | 424/261 |
| 4,198,391 | 4/1980 | Grainger | 424/37 |

OTHER PUBLICATIONS

WO80/01242 Jun. 26 1980, Franz et al., Galenical Preparation Solid Solution of Ergot Alkaloid in Gastric Juice Resistant Capsule 23 pp.

Primary Examiner—Shep K. Rose

Attorney, Agent, or Firm—Gerald D. Sharkin; Robert S. Honor; Thomas O. McGovern

[57] ABSTRACT

A stable ergot alkaloid soft gelatin capsule consisting essentially of a soft gelatin capsule shell and encapsulated therein a liquid center fill solution consisting essentially of a therapeutically effective amount of an ergot alkaloid of the formula

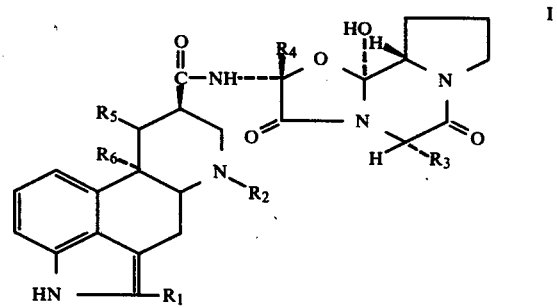

wherein
  $R_1$ is hydrogen or halogen,
  $R_2$ is hydrogen or $C_{1-4}$alkyl,
  $R_3$ is isopropyl, sec.-butyl, isobutyl or benzyl,
  $R_4$ is methyl, ethyl or isopropyl, and either
  $R_5$ is hydrogen and
  $R_6$ is hydrogen or methoxy or
  $R_5$ and $R_6$ together is an additional bond, or mixtures thereof, dissolved in a pharmaceutically acceptable polar, hydrophilic soft gelatin capsule center fill solvent.

25 Claims, No Drawings

SOFT GELATIN CAPSULE WITH A LIQUID ERGOT ALKALOID CENTER FILL SOLUTION AND METHOD OF PREPARATION

This invention relates to the administration of an ergot alkaloid or a pharmacologically acceptable acid addition salt thereof or mixtures thereof in a soft-gelatin capsule.

More particularly, it relates to a stable soft-gelatin capsule and a method of preparing a soft-gelatin capsule containing as its active ingredient an ergot alkaloid or a pharmaceutically acceptable acid addition salt thereof or mixtures thereof.

The advantages of administering pharmaceuticals in the form of soft-gelatin capsules are described in detail in the literature, for example, SOFT ELASTIC GELATIN CAPSULES: A UNIQUE DOSAGE FORM; William R. Ebert; Pharmaceutical Technology; October, 1977. Amongst the advantages are the benefits of a liquid form and the convenience of a solid dosage form and greater resistance to both oxidation and light degradation. Ergot alkaloids are especially sensitive to both of these types of degradation and would seem an ideal candidate for soft gelatin encapsulation. It has not been possible, however, to administer ergot alkaloids and their salts in this form because of the apparent instability of these alkaloids in acceptable solvents for the capsule fill, i.e., the solution which is encapsulated in the soft gelatin capsule shell. Ethanol, glycerine and propylene glycol do enhance the stability of ergot alkaloids in solution, but ethanol or glycerine and propylene glycol, by themselves, cannot be used as the soft gelatin capsule fill vehicle, because they attack and dissolve the capsule shell. In polyethylene glycols, which do not attack the capsule shell, studies show that the ergot alkaloids are extremely unstable. The cause of this instability is not known but was thought to be the result of some interaction between the ergot alkaloids and the polyethylene glycol, because the addition of stabilizers and anti-oxidants does not improve the stability of ergot alkaloids in this solvent. A 0.2% solution of a methanesulfonate salt of a 1:1:1 mixture by weight of dihydroergocryptine (2:1 $\alpha$:$\beta$), dihydroergocornine and dihydroergocristine in a polyethylene glycol 400 capsule fill containing 10% propylene glycol and 1.4% ascorbic acid was stored at ambient temperature in an amber bottle. At various intervals, the solution was assayed for ergot alkaloid content. The following results were obtained for the percentage of intact alkaloid:

| Time (weeks) | 0 | 1 | 4 | 7 | 15 |
|---|---|---|---|---|---|
| % retained | 98.3 | 92.7 | 88.4 | 79.7 | 71.3 |

For a commercially acceptable pharmaceutical product, a minimum of two years shelf-life stability with 90% and preferably 95% retention of undegraded ergot alkaloid is required. From the above data, it can be seen that the ergot alkaloid solution in polyethylene glycol and propylene glycol fail to meet this stability requirement after the first month of storage. Similar results are obtained in stability testing at higher concentrations of ergot alkaloids and lower concentrations of ascorbic acid. It is obvious from these results why an ergot alkaloid soft gelatin capsule has not heretofore been available commercially.

It has now been found that if the above ergot alkaloid solutions are encapsulated, there is surprisingly no further degradation of the alkaloid. More particularly, an ergot alkaloid solution identical to the one above containing 1.4% ascorbic acid and 0.2% ergot alkaloid was encapsulated immediately after preparation. The initial assay again indicated that 98.3% of the theoretical amount of alkaloid was present; and after 15 weeks storage at ambient temperature, the assay indicated that 98.2% of the original amount of alkaloid was still retained. Similarly, fill solutions containing 0.5 milligrams of ergot alkaloid and 0, 0.5 and 1.5% ascorbic acid lost approximately 10% of the alkaloid after one month storage in amber bottles; but following encapsulation, there was essentially no further loss of alkaloid.

Accordingly, the present invention provides a process for preparing a stable ergot alkaloid, soft gel capsule which comprises the steps of dissolving a therapeutically effective amount of an ergot alkaloid of the formula:

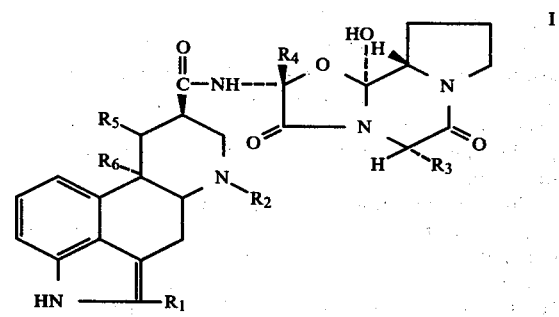

wherein
$R_1$ is hydrogen or halogen,
$R_2$ is hydrogen or $C_{1-4}$alkyl,
$R_3$ is isopropyl, sec.-butyl, isobutyl or benzyl,
$R_4$ is methyl, ethyl or isopropyl, and either
$R_5$ is hydrogen and
$R_6$ is hydrogen or methoxy or
$R_5$ and $R_6$ together is an additional bond,
or mixtures thereof, in a pharmaceutically acceptable polar, hydrophilic soft gelatin capsule center fill solvent to prepare a soft gelatin capsule center fill solution; and thereafter encapsulating the center fill solution obtained in a soft gelatin capsule shell before the percent of ergot alkaloid drops below 90% of the original therapeutically effective amount.

In this specification, the term "stable soft gelatin ergot alkaloid capsule" means that the capsule retains at least 90% of its original undegraded ergot alkaloid content for a minimum of 2 years when stored at ambient temperature.

When $R_1$ is halo, it is preferably bromine.

Preferred compounds of formula I are those in which $R_1$, $R_5$ and $R_6$ are hydrogen, $R_2$ is methyl, and $R_4$ is isopropyl or methyl, provided that $R_4$ is methyl only when $R_3$ is benzyl.

Particularly preferred compounds in which $R_2$ is methyl and $R_1$, $R_5$ and $R_6$ are hydrogen are dihydro-$\alpha$-ergocryptine ($R_4$=isopropyl, $R_3$=isobutyl), dihydro-$\beta$-ergocryptine ($R_4$=isopropyl, $R_5$=sec.-butyl), dihydroergocornine ($R_4$=$R_3$=isopropyl), dihydroergocristine ($R_4$=isopropyl, $R_3$=benzyl) and dihydroergotamine ($R_4$=methyl, $R_3$=benzyl), together with their salt forms. The preferred compound in which $R_1$ is bromine is bromocryptine, $R_2$=methyl, $R_3$=isobutyl, $R_4$=isopropyl and $R_5$ and $R_6$ are a second bond. Suitable salt forms are salts of pharmacologically acceptable acids, for example, the methanesulfonate, maleate and tartrate salt forms.

Particularly preferred are the methanesulfonate salt of dihydroergotamine (DHE) and the aforementioned methanesulfonate salt of a 1:1:1 mixture by weight of dihydroergocryptine (2:1 α.β), dihydroergocornine and dihydroergocristine (ergoloid mesylates).

As indicated above, the use of ergot alkaloids as pharmaceutical agents is well known and described in great detail in the literature, e.g., in the comprehensive survey ERGOT ALKALOIDS AND RELATED COMPOUNDS; B. Berde and H. O. Schild; Springer Verlag; Berlin, Heidelberg, NY, 1978. Ergoloid mesylates may, for example, be used in the treatment of conditions arising from cerebral vascular insufficiency and arteriosclerosis. A recommended oral dosage is 0.5 to 1.5 milligrams, preferably 1 milligram two to three times daily. As is also well known, dihydroergotamine is indicated, for example, in the treatment of orthostatic hypotension and the prophylaxis of migraine. Suitable oral dosages are from 0.5 to 3 milligrams of dihydroergotamine two to three times daily. Bromocryptine (2-bromo-α-ergocryptine) is used in the treatment of amenorrhea galactorrhea, and a suitable dosage is 1 to 3 milligrams two to three times daily.

The major proportion of the center fill solvent which is used in the present invention is a water-miscible, non-volatile, liquid polyethylene glycol selected from polyethylene glycols having a molecular weight from 200 to 600, or mixtures thereof. A particularly suitable polyethylene glycol is one having a molecular weight of 400 (PEG 400). The amount of polyethylene glycol must, at a minimum, be sufficient to dissolve the ascorbic acid employed in the capsule fill which, in turn, will depend on the amount of ergot alkaloid which is to be encapsulated. The maximum preferred capsule fill volume is 0.5 milliliters and 0.2 milliliters is especially preferred. Larger volumes result in capsule which are more difficult to swallow and lessens the gelatin capsule's ease of swallowing advantage over tablets and hard shell capsules.

The center fill solvent can also contain up to 10% and preferably 5% glycerine by volume or up to 10% propylene glycol by volume as a cosolvent. The filler vehicle can also contain pharmaceutically acceptable amounts of pharmaceutically acceptable acetylated glycerides and surfactants. Normally, such glycerides and surfactants are used in amount up to 30% by volume.

The center fill solution can also contain ascorbic acid to reduce degradation prior to and during encapsulation. It is preferred that the present center fill solution contain about 0.5 to 1.5%, preferably 1.5%, weight to volume of ascorbic acid for optimum protection.

The center fill solution is prepared by dissolving the ascorbic acid in about three quarters of the polyethylene glycol plus the cosolvents at a temperature of from 40° to 50° C. The temperature should not be allowed to exceed 50° C. The solution is cooled to 20° to 25° C. and the ergot alkaloid is added. The mixture is stirred until the ergot alkaloid dissolves, following which polyethylene glycol is added to bring the solution to the proper volume. The solution is then encapsulated before the percent of ergot alkaloid drops below 90% of its original contents. It is preferred that the center fill solution be encapsulated within 72 hours, preferably 24 hours, of its preparation to prevent the ergot alkaloid content from dropping below 95% of its initial content.

The gelatin capsule shell formulation is prepared according to well known procedures from gelatin, plasticizers, such as glycerine or sorbitol, and water. Additives such as coloring and flavoring agents; preservatives, for example, methyl and propylparaben or sorbic acid; and opacifiers, such as titanium dioxide, can also be included in the formulations. The hardness of the capsule is controlled by the amount of plasticizer; and for the soft-gelatin capsule of the present invention, the ratio of gelatin to plasticizer is preferably about 1:0.5 to 1:1; and the water to gelatin ratio in the wet capsule shell formulation is preferably about 0.75:1 to 1:1. The shell formulation is rolled into ribbons and the ergot alkaloid capsule fill is encapsulated in the shell formulation in the desired size and shape on a rotary die encapsulating machine in accordanc with standard techniques. The capsules are dried preferably at room temperature to equilibrium with 20 to 30% relative humidity.

EXAMPLE 1

In accordance with the procedure described above, a series of soft gelatin capsule center fills were prepared with ergoloid mesylate as the ergot alkaloid component. The various preparations were stored in amber bottles at room temperature prior to encapsulation. Capsules prepared from the capsule fills contained the following ingredients in the amounts indicated.

| Ingredient | Formulation | | | | |
| --- | --- | --- | --- | --- | --- |
| | A | B | C | D | E |
| Ergoloid Mesylate (mg.) | 1.0 | 1.0 | 1.0 | 1.0 | 1.0 |
| Ascorbic Acid (mg.) | — | — | 1.0 | 3.0 | 7.0 |
| Propylene Glycol (ml.) | — | 0.02 | 0.02 | 0.02 | 0.05 |
| PEG 400 (q.s.) | 0.2 | 0.2 | 0.2 | 0.2 | 0.5 |

Formulations A to D were encapsulated in #4 oval "B" opaque blue capsules approximately 3 weeks after preparation; and Formulation E was encapsulated in #9.5 oblong "A" opaque off-white capsules immediately after preparation.

The capsules were stored at room temperature and inspected at various intervals for degradation. The following assay results were obtained for the percentage of theoretical alkaloid retained at these intervals:

| | Retention of Alkaloid | | | | |
| --- | --- | --- | --- | --- | --- |
| | A | B | C | D | E |
| Initial Assay (%) | 98.5 | 101.1 | 98.8 | 98.0 | 98.3 |
| Filling Assay (%) | 89.0 | 88.0 | 90.4 | 93.6 | 98.3 |
| Encapsulation Assay after ~ 5 weeks | 89.0 | — | — | — | 98.2 |
| Encapsulation Assay after ~ 30 mos. | 90.0 | 91.5 | 94.3 | 92.7 | — |

From the above results, it can be seen that after approximately four weeks, the stability of the unencapsulated fill solutions falls below the minimum 90% retention of undegraded alkaloid level. In order to maintain retention above this level, the fill solution must be encapsulated prior to this time. In order to maintain the desired 95% retention level, it is estimated that the fill solution must be encapsulated no later than 72 hours after encapsulation.

Accelerated aging studies at 50, 60, 70 and 80° C. were carried out to determine the shelf life of Formulation E. The results show that the concentration of ergoloid mesylate in Formulation E would drop to the minimum permissible 90% level in 4 years at 30° C. and five and one-half years at 25° C. It is estimated that it would take capsules containing Formulation E approximately three and one-half years to drop to 95% of original concentration level at room temperature.

EXAMPLE 2

In an appropriate vessel a mixture of 3000 milliliters of PEG 400 and 400 milliliters of propylene glycol is heated to 45° C. to 50° C. In this mixture, 56 grams of ascorbic acid are dissolved with stirring, after which the solution is cooled to 20° to 25° C. To this is added 8.15 grams of ergoloid mesylates (98.1% assay). The mixture is stirred until the alkaloid is completely dissolved, at which point PEG 400 is added to bring the formulation to a final volume of 4000 milliliters. The formulation is encapsulated within 24 hours in #9.5 oblong "A" off-white opaque capsules and packaged. The finished product possesses all of the advantages of a soft gelatin capsule and has a 95% shelf-life stability in excess of three years.

When 16 grams of dihydroergotamine as the methanesulfonate or 20 grams of 2-bromo-α-ergocryptine as the methanesulfonate is used in place of the ergoloid mesylates above, there is obtained a soft-gelatin capsule with equivalent shelf-life stability containing these ergot alkaloids.

EXAMPLE 3

In an appropriate vessel a mixture of 1500 milliliters of PEG 400 and 200 milliliters of propylene glycol is heated to 45° C. to 50° C. In this mixture, 30 grams of ascorbic acid are dissolved with stirring, after which the solution is cooled to 20° to 25° C. To this is added 10.11 grams of ergoloid mesylates (98.1% assay). The mixture is stirred until the alkaloid is completely dissolved, at which point PEG 400 is added to bring the formulation to a final volume of 2000 milliliters. The formulation is encapsulated within 24 hours in opaque blue capsules and packaged. The finished product possesses all of the advantages of a soft gelatin capsule and has a 95% shelf-life stability in excess of three years.

What we claim is:

1. A method of preparing a stable ergot alkaloid soft gelatin capsule which comprises the steps of dissolving a therapeutically effective amount of a ergot alkaloid of the formula

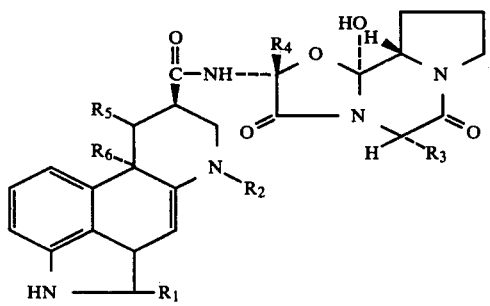

wherein
$R_1$ is hydrogen or halogen,
$R_2$ is hydrogen or $C_{1-4}$alkyl,
$R_3$ is isopropyl, sec.-butyl, isobutyl or benzyl,
$R_4$ is methyl, ethyl or isorpropyl, and either
$R_5$ is hydrogen and
$R_6$ is hydrogen or methoxy or
$R_5$ and $R_6$ together is an additional bond,
or mixtures thereof, in a pharmaceutically acceptable polar, hydrophilic soft gelatin capsule center fill solvent to prepare a liquid soft gelatin capsule center fill solution; and thereafter encapsulating the center fill solution obtained in a soft gelatin capsule shell before the percent of ergot alkaloid drops below 90% of the original therapeutically effective amount.

2. A method according to claim 1 in which the center fill solution is encapsulated within 72 hours after preparation.

3. A method according to claim 1 in which the center fill solution is encapsulated within 24 hours after preparation.

4. A method according to claim 1 in which the ergot alkaloid is 0.5 to 6 milligrams of ergoloid mesylates.

5. A method according to claim 1 in which the ergot alkaloid is 0.5 to 3 milligrams of dihydroergotamine mesylate.

6. A method according to claim 1 in which the ergot alkaloid is 1 to 3 milligrams of bromocryptine mesylate.

7. A method according to claim 1 in which the center fill solution contains about 0.5 to 1.5% weight to volume ascorbic acid.

8. A method according to claim 1 in which the center fill solution contains about 1.5% weight to volume ascorbic acid.

9. A method according to claim 1 in which the center fill solvent is polyethylene glycol with a molecular weight of from about 200 to 600.

10. A method according to claim 9 in which the center fill solvent is polyethylene glycol with a molecular weight of about 400.

11. A method according to claim 10 in which the center fill solvent contains about 10% by volume propylene glycol.

12. A stable ergot alkaloid soft gelatin capsule consisting essentially of a soft gelatin capsule shell and encapsulated therein a liquid center fill solution consisting essentially of a therapeutically effective amount of an ergot alkaloid according to claim 1 dissolved in a pharmaceutically acceptable polar, hydrophilic, soft gelatin capsule center fill solvent.

13. A capsule according to claim 12 in which the ergot alkaloid is 0.5 to 6 milligrams of ergoloid mesylates.

14. A capsule according to claim 12 in which the ergot alkaloid is 0.5 to 3 milligrams of dihydroergotamine mesylate.

15. A capsule according to claim 12 in which the ergot alkaloid is 1 to 3 milligrams of bromocryptine mesylate.

16. A capsule according to claim 12 in which center fill solution contains about 0.5 to 1.5% weight to volume ascorbic acid.

17. A capsule according to claim 12 in which the center fill solution contains about 1.5% weight to volume ascorbic acid.

18. A capsule according to claim 12 in which the center fill solvent is polyethylene glycol with a molecular weight of from about 200 to 600.

19. A capsule according to claim 18 in which the center fill solvent is polyethylene glycol with a molecular weight of about 400.

20. A capsule according to claim 19 in which the center fill solvent contain about 10% by volume propylene glycol.

21. A capsule according to claim 12 in which the liquid center fill solution consists essentially of 1 milligram of ergoloid mesylates or dihydroergotamine mesylate or 2.5 milligrams of bromocryptine mesylate, 7 milligrams of ascorbic acid, 0.05 milliliters of propylene glycol and an amount of polyethylene glycol with a molecular weight of about 400 to bring the center fill solution volume to about 0.500 milliliters.

22. A capsule according to claim 20 in which the soft gelatin capsule shell is #9.5 oblong "A" off-white opaque capsule shell.

23. A capsule according to claim 12 in which the liquid center fill solution consists essentially of 1 milligram of ergoloid mesylates, 3 milligrams of ascorbic acid, 0.02 milliliters of propylene glycol and an amount of polyethylene glycol 400 to bring the center fill solution volume to about 0.200 milliliters.

24. A capsule according to claim 23 in which the soft gelatin capsule shell is a #4 oval "B" opaque blue capsule shell.

25. A capsule according to claim 21 in which the liquid center fill solution consists essentially of 1 milligram of ergoloid mesylates, 7 milligrams of ascorbic acid, 0.05 milliliters of propylene glycol and an amount of polyethylene glycol with a molecular weight of about 400 to bring the center fill solution volume to about 0.500 milliliters.

* * * * *